United States Patent [19]

Lisiecki et al.

[11] Patent Number: 4,519,398
[45] Date of Patent: May 28, 1985

[54] METHOD AND APPARATUS FOR LONG-TERM MONITORING OF PHYSIOLOGICAL ACTIVITY TO PROVIDE A COMPACT PORTABLE RECORD

[75] Inventors: Andrew I. Lisiecki, Irvine; Alan S. Wong, Escondido, both of Calif.

[73] Assignee: Del Mar Avionics, Irvine, Calif.

[21] Appl. No.: 341,309

[22] Filed: Jan. 21, 1982

Related U.S. Application Data

[63] Continuation of Ser. No. 55,384, Jul. 9, 1979, abandoned.

[51] Int. Cl.³ .............................................. A61B 5/04
[52] U.S. Cl. ................................. 128/710; 346/33 ME
[58] Field of Search ................. 346/33 ME; 128/690, 128/695, 696, 702, 703, 704, 706, 710, 711, 736

[56] References Cited

U.S. PATENT DOCUMENTS

| | | | |
|---|---|---|---|
| 4,053,951 | 10/1977 | Hudspeth et al. | 128/736 |
| 4,096,866 | 6/1978 | Fischell | 128/419 PG |
| 4,193,393 | 3/1980 | Schlager | 128/710 |
| 4,197,850 | 4/1980 | Schulman et al. | 128/419 PG |
| 4,211,238 | 7/1980 | Shu et al. | 128/711 |
| 4,250,888 | 2/1981 | Grosskopf | 128/702 |

FOREIGN PATENT DOCUMENTS

225033 12/1958 Australia ................. 128/419 PS

Primary Examiner—William E. Kamm
Attorney, Agent, or Firm—Beehler, Pavitt, Siegemund, Jagger & Martella

[57] ABSTRACT

The system enables ambulatory monitoring of a patient's blood pressure and heart rate without the need for the patient to wear a portable magnetic tape recorder. The system takes the place of the tape recorder. ECG electrodes and a blood pressure cuff are affixed to the patient and are connected to a blood pressure measuring apparatus worn by the patient. The Data Acquisition and Storage System (DAS) is connected to the blood pressure measuring apparatus and includes a solid state storage device in which the successive measurements are stored. After the monitoring session, which may last 24 hours, the patient returns to the clinic, where the DAS is connected to a stationary charter that prints and plots the stored data in tabular and graphical form. The DAS includes a clock for determining the time of day at which the successive blood pressure readings are taken, and these times are stored along with the data. The clock is kept running even when the blood pressure measuring apparatus is disconnected from the DAS, so that when connection is reestablished the elapsed time can be determined. The clock also permits the heart rate to be determined and stored by the DAS. In the event the voltage of the source that powers the DAS should fall below a preset level, the DAS goes into a dormant mode to conserve power and prevent erroneous calculations. In the dormant mode the data stored in the solid state storage device is preserved.

8 Claims, 9 Drawing Figures

Fig. 4 — DATA ACQUISITION AND STORAGE SYSTEM BLOCK DIAGRAM

Fig. 9

METHOD AND APPARATUS FOR LONG-TERM MONITORING OF PHYSIOLOGICAL ACTIVITY TO PROVIDE A COMPACT PORTABLE RECORD

This is a continuation of application Ser. No. 055,384, filed July 9, 1979, now abandoned.

BACKGROUND OF THE INVENTION

1. Field of the Invention

The present invention is in the field of medical electronics, and more specifically, relates to a compact, battery-operated data acquisition and storage device to be worn by ambulatory patients to facilitate physiological assessment of the condition of cardiac or hypertensive patients. Although the present invention has no moving parts, it performs all the functions of and replaces the portable tape recorder generally used in the art of ambulatory monitoring.

2. The Prior Art

In ambulatory monitoring as normally practiced, the patient wears a device for measuring or sensing the physiological variables to be monitored, such as ECG waves, EEG waves, blood pressure, heart rate, etc. As practiced in the prior art, the patient also wears a miniaturized portable magnetic tape recorder which records the successive values of the physiological signal obtained from the sensors. After the recording session, which may last twenty-four hours or more, the magnetic tape is returned to the clinic where the tape is played back on suitable equipment so that the signals can be recovered and analyzed. The signals from the playback apparatus are typically applied to the printer-plottor or charter which produces a graphical chart record, as well as numerical data.

Various factors limit the ability of the designers of the tape recorder to reduce its weight and size, these being primarily the amount of continuous data recorded and the necessity of accurate reproduction of continuous analog information such as ECG waveforms from the recording into diagnostic quality results. Even though the recording speed for ECG waveforms is made relatively slow in order to sufficiently compact the data, the tape requires considerable length and space. Sufficient battery must be provided to power the tape-drive motor reliably for the entire duration of the monitoring session, and this adds considerable weight. The tape-drive motor normally includes heavier ferromagnetic elements. Such tape recorders are highly developed and sophisticated instruments designed to do their job with a minimum of weight, but nevertheless, even if not burdened with recording of continuous waveforms over a long recording period, such recorders are complicated and are subject to wear of moving parts. Also, the portable magnetic tape recorder tends to be expensive to produce because it must be carefully engineered to minimize power consumption and to operate extremely quietly. A less expensive acceptable substitute would be highly desirable.

An acceptable substitute for the magnetic tape recorder that could accomplish quality recording while having no moving parts, no noise, and high reliability would be considered a worthwhile advance in the art.

Contemporary playback apparatus used to recover long-term recorded ECG and blood pressure data from magnetic tapes is typically very sophisticated. To save time, the apparatus is made capable of playing back the tape at a higher speed than the speed at which it was recorded and of analyzing the data on the tape as the tape is played back. The operator can select the type of analysis he prefers. The more sophisticated analyzers can recognize the occurrence of waveforms associated with a number of heart disorders and can display the data in ways which facilitate closer study of the more interesting cardiac episodes. A contemporary apparatus for playback and analysis of the recorded tapes is described in U.S. Pat. No. Re. 29,921, reissued Feb. 27, 1979 to Isaac R. Cherry and Donald L. Anderson for "Electrocardiographic Computer."

Clearly, if the magnetic tape could be eliminated, the need for at least the mechanical variable-speed tape playback portion of the analyzer would also be eliminated. Until the present invention, there existed no satisfactory substitute for the magnetic tape and its associated recorder and playback equipment in long-term cardiac monitoring. The present invention changed this situation by demonstrating an advantageous substitute for the magnetic tape system which should show the way for future development of the ambulatory monitoring art.

Prior to summarizing the innovative aspects of the present invention, the equipment with which it will be used will be described briefly. That equipment includes: blood pressure measuring apparatus for ambulatory patients, available under the registered trademark PRESSUROMETER® II from the assignee of the present invention, Del Mar Avionics, of Irvine, Calif.; a magnetic tape recorder for ambulatory patients known as the Del Mar Avionics Model 447; and an intelligent printer-plotter known as the PRESSUROMETER® CHARTER, available from the same source. Readers familiar with instruments of these types may choose to turn directly to the section entitled "Summary of the Invention."

Ambulatory Blood Pressure Measuring Apparatus

The blood pressure measuring apparatus with which the data acquisition and storage system of the present invention is used is described in U.S. patent application Ser. No. 796,893 filed May 17, 1977 by W. David Squires, Donald L. Anderson and Isaac Raymond Cherry for "Blood Pressure Monitoring System", the disclosure of which is incorporated herein by reference. The blood pressure measuring apparatus operates on the auscultation method, employing a pressurizable cuff and requiring no intervention by the patient. ECG signals are sensed by ECG electrodes, and a microphone is used to sense the Korotkow sounds as the pressure in the cuff is varied. The presence or absence of a Kortokow sound within a preset interval following each heart beat is used in determining when the cuff pressure successively equals the systolic and diastolic pressures. Those pressures are determined in each cycle of operation and are recorded on a continuously-running portable tape recorder, along with the ECG signals.

In each cycle of operation of the blood pressure monitoring system, the initial pressure to which the cuff is inflated is based on the systolic pressure measured in the immediately preceding cycle. The pressure in the inflated cuff is thereafter stepped downward in small discrete decrements triggered by successive R-waves of the ECG signal during the measurement phase of each cycle. After both the systolic and diastolic pressures have been determined, the remaining cuff pressure is vented through the same valve that was used to produce the stepwise pressure reduction. After a number of cycles of operation, the magnetic tape is removed from the portable recorder and inserted into an analyzer for high-speed playback and automated plotting of the heart rate and accompanying blood pressure readings on a common chart.

Magnetic Tape Recorder

The magnetic tape recorder with which prior art data acquisition and storage systems were normally used is described in U.S. patent application Ser. No. 918,698 filed June 23, 1978 by Stephen K. Shu and W. David Squires for "Apparatus for Recording and Playing Back Electrocardial Signals", the disclosure of which is incorporated herein by reference. The tape recorder encodes and records the blood pressure measurements obtained from a patient on a particular track on a two-track magnetic tape, and a channel of continuous ECG signals are are also recorded on the same track as the blood pressure data, along with time-of-day-signals and event-marker signals. The ECG signal is recorded in analog form, but the other signals are recorded as pulse-coded signals, each coded in its own format. The other track of the two-track tape is dedicated to an uninterrupted recording of a continuous ECG signal.

The Charter

The stationary charter with which the portable blood pressure measuring apparatus and the portable data acquisition and storage system of the present invention are normally used is described in U.S. patent application Ser. No. 959,091 filed Nov. 9, 1978 for "Charter With Automatic Editing" by John A. Ripley, Donald C. Woods, and James Kaine. As disclosed therein, the charter is an intelligent printer-plotter for use with a source of time-correlated digital systolic and diastolic blood pressure data and heart rate date. The source may also include coded time signals and event-marker signals. After the conclusion of the monitoring session, when it is desired to transfer the data from the portable apparatus into the charter for plotting, the portable apparatus is brought to the location of the stationary charter, and the data acquisition and storage system is then connected electrically to the charter. Power is then applied to the charter, and the DATA LOAD button on the charter is depressed. This causes the charter to generate a SERVICE REQUEST signal which the charter applies to the data acquisition and storage system. The data acquisition and storage system acknowledges the SERVICE REQUEST signal by applying to the charter a signal representing the number of valid data readings that are available for transfer. Only then is the digital data transferred from the data acquisition and storage system to the charter in response to a predetermined number of strobe pulses generated by the charter and applied to the DAS.

The charter receives, stores, analyzes, and edits the data, producing tables of data and graphs having a particular format. The charter smoothes the data by a moving average technique and includes modes which permit the operator to edit the data manually or to command the charter to perform the editing automatically. In the automatic editing mode, the data are tested against preestablished criteria designed to determine if the values of the variables are plausible. Data not meeting the criteria are flagged so they can be passed over in subsequent calculation and printing operations if that is desired; however, the flagged data is not destroyed, but is retained in a memory to permit subsequent re-examination and to permit verification of the editing process.

SUMMARY OF THE INVENTION

The Data Acquisition and Storage System (DAS) of the present invention has no moving parts and is a computerized substitute for the magnetic tape recorder of the prior art worn by the patient during ambulatory monitoring. The DAS functions like a magnetic tape recorder in that it stores the data for later read-out, it generates and stores a time signal so that the measurement times can be determined, and it protects against loss of the stored data in the event the power fails. However, compared with a magnetic tape recorder, the DAS has a number of unique advantages. From the standpoint of patient comfort, the DAS is lighter in weight than the recorder. Maintainability of the DAS should prove to be good because of the lack of moving parts and freedom from magnetic tape playback equipment.

The DAS is an active device having control and computational capabilities. These capabilities are exploited in a preferred embodiment of the present invention to calculate heart rate, to log time and to process heart rate, blood pressure and time signals from serial to parallel form and the like. The DAS in a preferred embodiment also performs certain control functions, such as testing the condition of its power source so that if the applied power is not adequate, the DAS enters a power-conserving mode in which the stored data is preserved. Further, the DAS includes a clock for determining the times at which the measurements are made. Thus, it is apparent that these control and computational capabilities distinguish the DAS from a simple solid state memory.

The novel features which are believed to be characteristic of the invention, both as to organization and method of operation, together with further objects and advantages thereof, will be better understood from the following description considered in connection with the accompanying drawings in which the preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
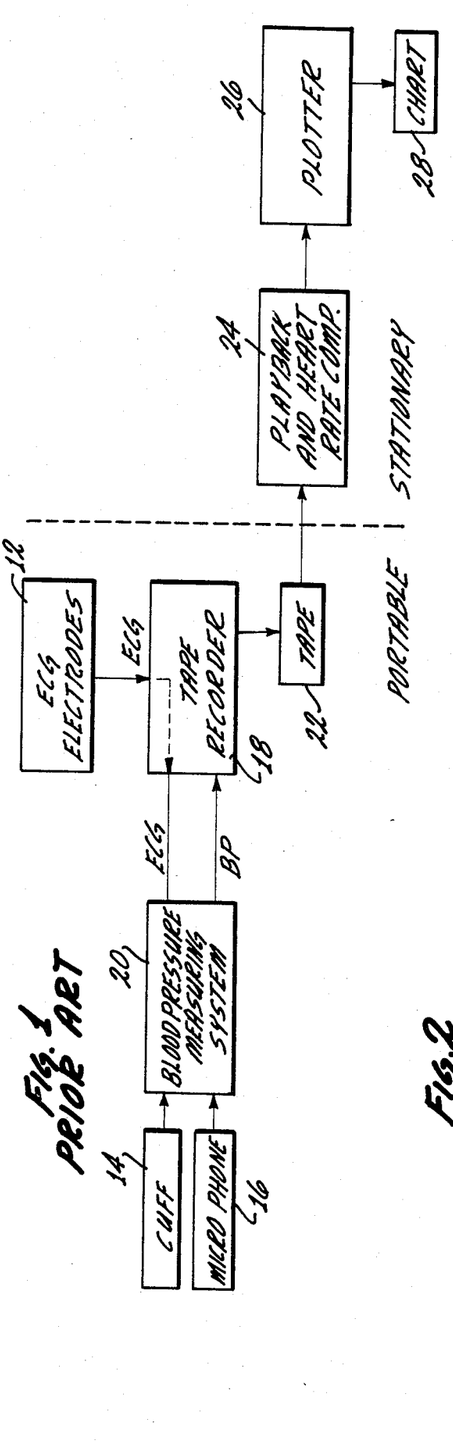
FIG. 1 is a block diagram of a prior art system used for obtaining and producing a chart of the blood pressure and heart rate of a patient during an ambulatory monitoring session.

Turning now to the drawings, in which like parts are denoted by the same reference numeral throughout, there is shown in FIG. 1 a prior art system for measuring, recording, playing back, and charting the blood pressure and ECG waveform of a patient. ECG electrodes 12, an inflatable cuff 14, and a microphone 16 are affixed to the patient's body at appropriate locations and with the microphone 16 positioned between the cuff 14 and the patient's arm. It is also necessary for the patient to wear a tape recorder 18 as well as a portable blood pressure measuring system 20. As shown in FIG. 1, the ECG electrodes 12 are connected directly to the tape recorder since one channel of the magnetic tape is dedicated to a particular channel of ECG signals. However, ECG signals are applied, as indicated, by the tape recorder to the blood pressure measuring system 20 for use in triggering a series of small pressure decrements in the cuff pressure. The blood pressure measuring system 20 determines in succession the systolic blood pressure and the diastolic blood pressure. The blood pressure data is encoded and applied to the portable magnetic tape recorder 18 which records the data on the magnetic tape 22. All of the components mentioned thus far are portable.

At the conclusion of the ambulatory monitoring session, the magnetic tape 22 is taken to the location of the stationary playback and charting equipment. The tape 22 is then inserted into the playback apparatus 24 which may also include circuitry for analyzing the ECG signal and determining the heart rate, the number of ectopic beats, and other desirable information. Electrical signals generated by the playback apparatus 24 represent the various quantities of interest, and these signals are applied to a plotter 26 which produces a chart 28 of the information. The playback apparatus 24 and the plotter 26 are stationary and are usually located in a clinic where they are operated by trained personnel.

Figure 2:
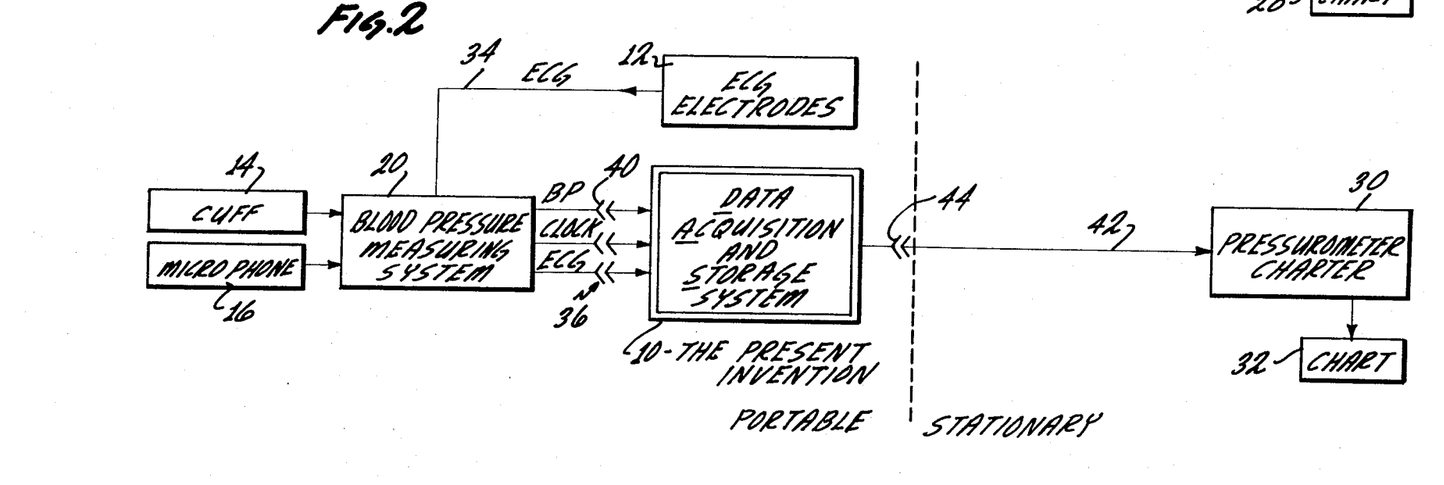
FIG. 2 is a block diagram of a system for obtaining and charting the blood pressure and heart rate of a patient in which the present invention is employed.

FIG. 2 is a block diagram of the system with which the Data Acquisition and Storage system (DAS) 10 of the present invention is used. In comparison to FIG. 1, it can be seen that the system of FIG. 2 also employs ECG electrodes 12, a cuff 14, and a microphone 16 all affixed to the patient as well as a portable blood pressure measuring system. The striking difference is that in the system of FIG. 2 the tape recorder 18, the magnetic tape 22, and the playback apparatus 24 have been replaced by the DAS 10 of the present invention. The charter 30 used in the system of FIG. 2 is a different device from the plotter 26 used with the system of FIG. 1, and likewise, the chart 32 produced by the charter 30 is significantly different.

The blood pressure measuring apparatus 20 of FIG. 2 is very similar to that used in the system of FIG. 1. Several minor modifications have been made to the blood pressure measuring apparatus to permit the ECG leads 34 to be connected directly to it and to bring a clock signal on one of the lines 36 from the blood pressure measuring apparatus 20 to the DAS 10. As noted above, the blood pressure measuring apparatus 20 and the charter 30 of FIG. 2 are the subject matter of copending applications, to which reference should be made for a fuller description. The present invention is the DAS 10 of FIG. 2.

Figure 3:
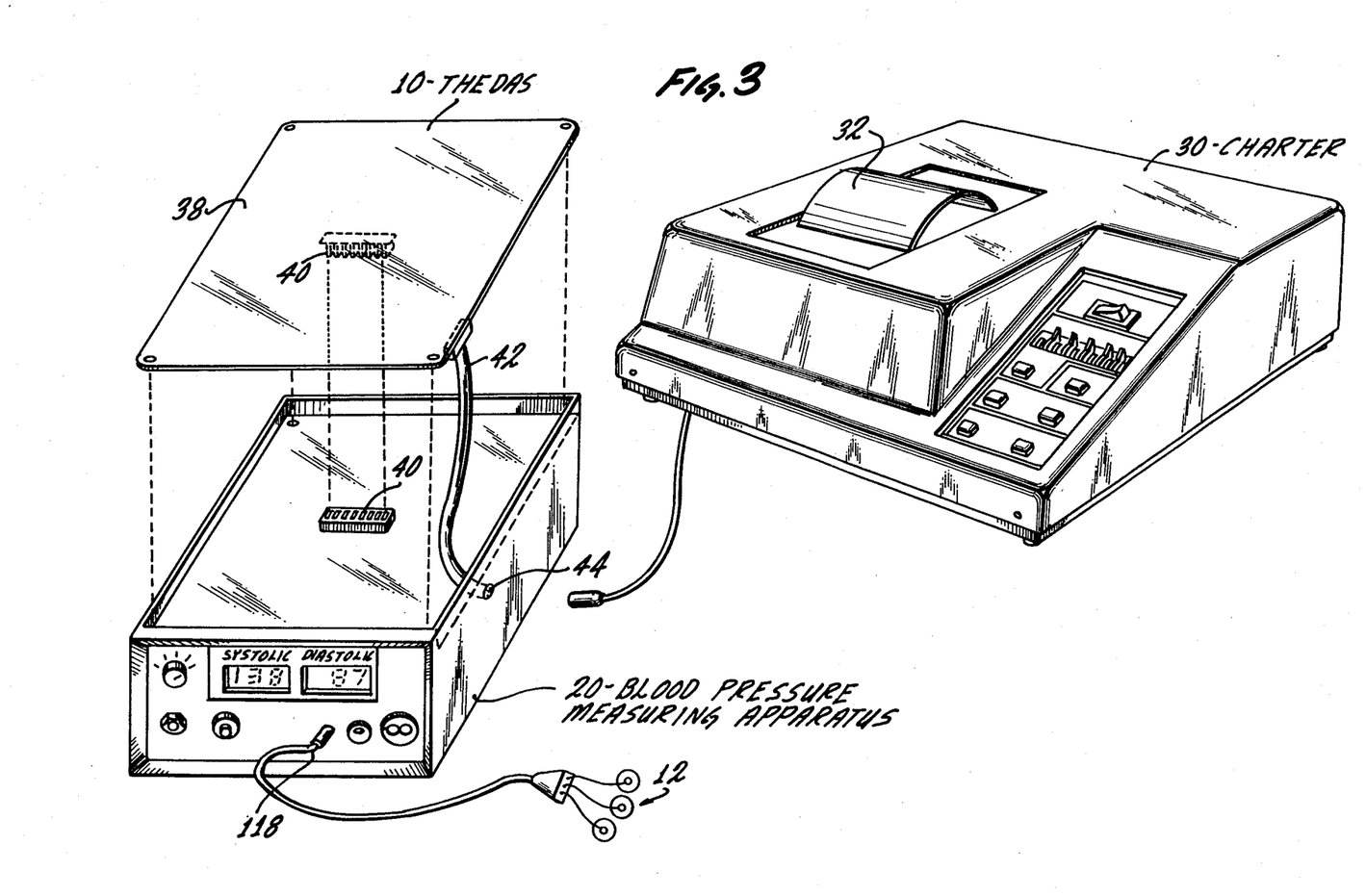
FIG. 3 is a perspective view showing the relationship of the present invention to the other apparatus with which it is used.

FIG. 3 is a perspective view showing the blood pressure measuring system 20, the charter 30, and the DAS 10. Physically, the DAS circuitry is mounted on a circuit board 38 which is attached to the blood pressure measuring apparatus 20 so as to become a part of it. The connector 40a and 40b provides the electrical interconnection between the blood pressure measuring apparatus 20 and the DAS 10, and the cable 42 serves as an electrical interconnection with the charter 30. The cable 42 is interrupted by the connector 44 to permit the portable components to be separated from the stationary charter 30.

Figure 4:
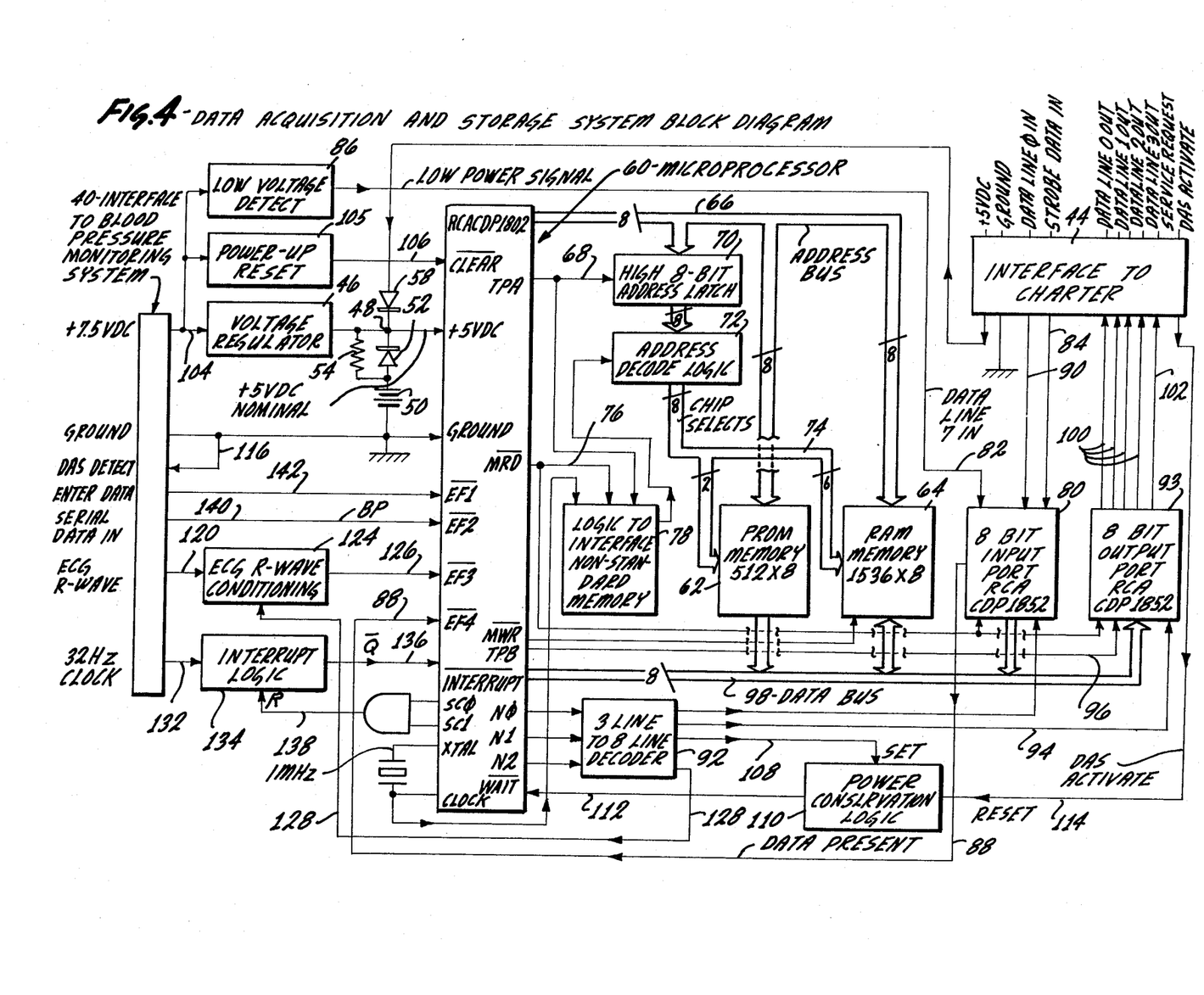
FIG. 4 is a block diagram showing a preferred embodiment of the data acquisition and storage system of the present invention.

FIG. 4 is a block diagram of a preferred embodiment of the DAS of the present invention. The current to operate the nominal +5 volt CMOS logic in its normal mode is derived from the nominal +7.5 VDC battery in the blood pressure measuring apparatus 20 and the interface connector 40 includes paths for the +7.5 DC supply as well as a ground return path. A voltage regulator 46 maintains the voltage at junction point 48 at +5 VDC. Operating current can also be supplied to junction point 48 from two other sources when the +7.5 VDC battery of the blood pressure measuring apparatus 20 is depleted or removed. Assuming that the DAS is not connected to the charter 30, the alternative battery power source 50 will automatically supply current to the junction 48 when the voltage at the junction drops to a value approximately 0.4 volts less positive than the auxiliary battery voltage, due to the forward voltage drop of the diode 52. The auxiliary battery 50 is trickle-charged through the resistor 54 whenever the voltage at the junction 48 exceeds the auxiliary battery voltage. The CMOS logic in the DAS will operate on voltages measured at the junction 48 as low as +3 VDC. Current can also be supplied to the junction 48 from the +5 VDC power supply in the charter 30 through the connector 44 via the line 56, the latter being connected to the junction 48 through the diode 58.

An eight-bit CMOS microprocessor 60 in conjunction with a firmware program contained in the Programmable Read Only Memory (PROM) 62 controls the data acquisition, storage, and communication functions of the DAS. In the preferred embodiment, the microprocessor 60 is a commercially available type known as an RCA CDP 1802. The microprocessor 60 addresses the PROM 62 and the Random Access Memory (RAM) 64 through an eight-line multiplexed address bus 66. The microprocessor control signal, "TPA", on the line 68 automatically latches the most significant eight bits of the sixteen-bit address into the address latch 70 at the proper time during the microprocessor instruction cycle. The three least significant bit lines from the address latch 70 are brought to the address decode logic 72 which selects 1 to 8 blocks of either PROM or RAM memory via the chip select lines 74. Each block of memory is organized into 256×8 bits. The time at which a block of memory is selected is different from the standard RCA system because of the utilization of latched-address PROM 62 and RAM 64 memories specific to the preferred embodiment. The high-to-low transition of the "$\overline{\text{MRD}}$" line 76 occurs when the memory address is not yet valid. In the DAS system, the high-to-low transition of the "$\overline{\text{MRD}}$" output signal is delayed by one microprocessor clock interval by the delay logic circuit 78. The output of the delay logic circuit 78 is connected to the address decode logic 72 and serves to activate one of the chip select lines 74.

The PROM 62 is a CMOS fusable-link-programmed memory organized in 2 blocks or pages of 256×8 bits, making a total of 512×8 bits for the program memory. The RAM 64 also is a CMOS memory organized in 6 blocks or pages of 256×8 bits, making a total of 1,536×8 bits of volatile storage memory. The PROM 62 and the RAM 64 send to and receive information from the microprocessor 60 via the 8-bit bi-directional data bus 98.

The microprocessor accepts four direct input lines labelled "$\overline{EF1}$", "$\overline{EF2}$", "$\overline{EF3}$", and "$\overline{EF4}$". These lines can be interrogated by software instructions to test directly whether a logic high level or a logic low level is present. In addition to these direct input lines, an 8-bit input port 80 is provided. Two input lines 82, 84 are connected to the input port 80. The lines 82 carries a "LOW POWER" signal from the Low Voltage Detect Circuit 86 to the input port 80. The "strobe data in" line 84 is a handshaking line by which the charter 30 signals the DAS by bringing the "strobe data in" line from a logic high level to a logic low level, thereby latching the input data bit on the line 90 into the input port 80. The input port responds to this external request by bringing the "data present" line 88, which is connected to the $\overline{EF4}$ input of the microprocessor 60, from a logic high to a logic low level. The program software then periodically polls the $\overline{EF4}$ line to ascertain whether the charter 30 is requesting data from the DAS. The input port is selected by the "$\overline{MRD}$" signal on the line 76 from the microprocessor 60 and the "input port select" line 90 from the decoder 92. The decoder 92 receives inputs from three microprocessor lines, "N0", "N1", and "N2", which are activated when certain software input or output instructions are executed. One of seven input or output function lines are selected by the 3-line-to-8-line decoder 92. Any one of the output lines from the 3-to-8 decoder 92, when selected, will output a logic high level pulse for the duration of seven microprocessor clock intervals (seven microseconds).

The eight-bit output port 93 is selected by the "output port select" line 94 and the microprocessor-generated control signal "TPB" on the line 96. The output port, in response to a software output instruction, latches eight bits of data from the data bus 98 and presents four of these bits to the charter 30 through the connector 44 on the four lines 100. In addition, the output port generates a logic high pulse on the "service request" line 102 of duration eight microprocessor clock cycles (eight microseconds). The "service request" output signifies to the charter 30 that four bits of data are valid on the data lines 100.

The Power-up Reset Circuit 105 generates a logic low pulse only when a new battery has been installed in the blood pressure measuring apparatus 20 and the +7.5 VDC voltage input on the power conductor 104 changes from zero volts to +7.5 VDC. The microprocessor 60 receives this pulse at its "$\overline{CLEAR}$" input via the line 106 and executes an internal reset sequence including starting to execute the program stored in the PROM 62 at address location zero. If the +7.5 VDC battery voltage should decrease to zero, the DAS will continue to operate on the auxiliary battery 50. The Low Voltage Detect Circuit 86 senses when the +7.5 VDC voltage input drops below approximately +5 VDC. When this condition occurs, the line 82 changes from a logic high level to a logic low level which is the "LOW POWER" signal applied on the line 82 to the eight-bit input port 80. The software program polls this input line periodically, and if it ever is found to be at a logic low level, the program branches to a power-conservation subroutine. This subroutine via an output instruction sends a seven microsecond pulse on the "power down" line 108 which sets a flip-flop in the Power Conservation Logic Circuit 110. The logic low level inverted output of the flip-flop is connected to the "$\overline{WAIT}$" input of the microprocessor 60 via the line 112. A logic low level on the "$\overline{WAIT}$" line puts the microprocessor 60 into a "pause mode" which halts all internal microprocessor operations except the internal clock operation. This has the result of reducing the DAS current consumption to less than 300 microamps. A "DAS ACTIVATE" signal from the charter 30 on the line 114 is used to reset the flip-flop in the Power Conservation Logic circuit 110. When the "$\overline{WAIT}$" line is brought to the logic high level, the microprocessor 60 resumes program execution at exactly the location in the microprocessor cycle that it left off when put into the "pause mode".

Figure 5:
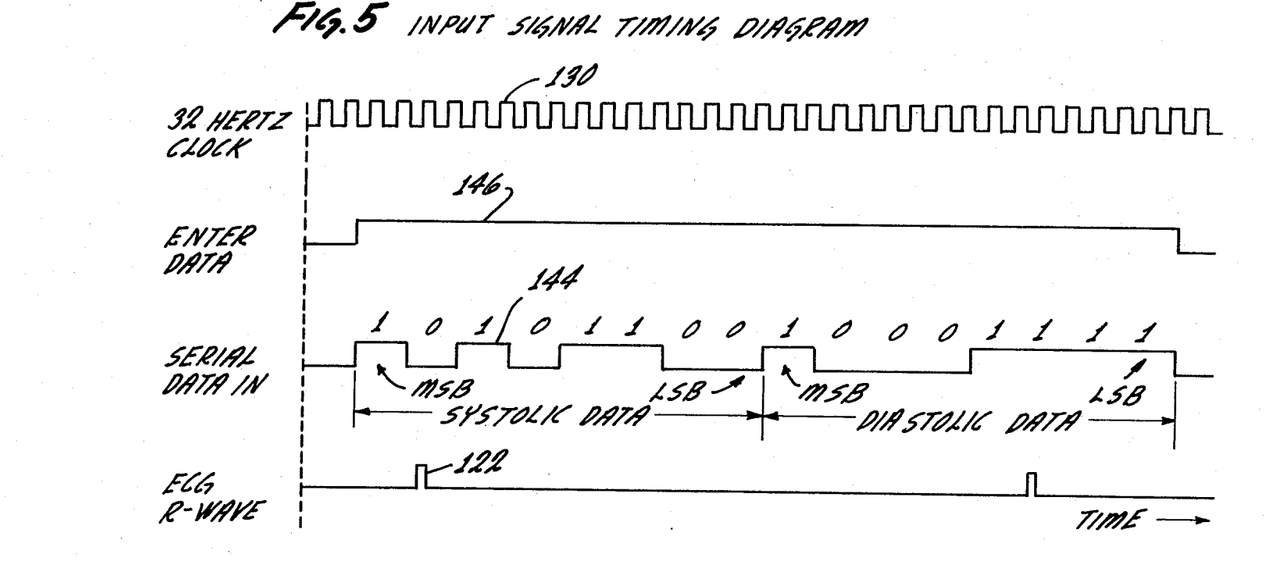
FIG. 5 is a graph showing the waveforms of certain signals of a function of time, are used in a preferred embodiment at FIG. 4.

A "DAS DETECT" signal on the line 116 is sent to the blood pressure measuring apparatus 20 where it is used to control an analog gate which disables the blood pressure measuring apparatus 20 from sending output signals to the recorder jack 118 of FIG. 3, and allows continuous ECG information to be input through that jack from the patient's electrodes 12 of FIG. 3. The ECG signal is conditioned in the blood pressure measuring apparatus 20 as described in the aforementioned pending patent application, and the ECG signal is presented to the DAS on the "ECG R-wave" line 120. FIG. 5 illustrates the "ECG R-wave" waveform 122 which consists of logic high level pulses of approximately 20 milliseconds duration, with the leading edge of each pulse corresponding to the occurrence of the R-wave. These pulses are applied to the ECG R-wave conditioning circuit 124.

The leading edge of the "ECG R-wave" waveform 122 sets a flip-flop in the ECG R-wave conditioning circuit 124, and the output of the flip-flop is connected via the line 126 to the microprocessor 60 flag input "$\overline{EF3}$". The software interrogates "$\overline{EF3}$" to detect the occurrence of an R-wave and resets the flip-flop of the ECG R-wave conditioning circuit 124 via an output instruction which generates a signal applied to the decoder 92 which generates a pulse on the "R-wave reset line" 128.

The "32 Hz clock" signal 130 of FIG. 5 is a crystal-controlled timing signal generated in the blood pressure measuring apparatus 20 and brought into the DAS on the line 132 of FIG. 4. The rising edge of this signal sets a flip-flop in the Interrupt Logic Circuit 134, which generates a logic low level and applies it to the "$\overline{Interrupt}$" input of the microprocessor 60 via the line 136. When the microprocessor 60 acknowledges the interrupt, it generates an "INTERRUPT RESET" signal on the line 138, that resets the flip-flop of the Interrupt Logic Circuit 134 in readiness for the next interrupt.

Blood pressure data is presented to the microprocessor 60 at its "$\overline{EF2}$" input via the "serial data in" line 140. Referring to FIG. 5, the blood pressure information is transmitted as a 16-bit serial binary bit stream 144 on the "serial data in" line 140. The systolic blood pressure is transmitted first with the most significant bit first, followed by the diastolic blood pressure with its most significant bit first.

Transfer of the blood pressure data from the blood pressure measuring apparatus 20 into the DAS is initiated by an "ENTER DATA" signal 146 of FIG. 5, on the "enter data" line 142. The "ENTER DATA" signal 146 is identical to the DATA VALID signal referred to in the co-pending application on the blood pressure measuring apparatus. When the "ENTER DATA" line 142 goes to a logic high level, the first blood pressure bit is valid on the rising edge of the "32 Hz clock" signal 130 and is presented on the "serial data in" line 140. Succeeding data bits are valid on every other rising edge of the "32 Hz clock" line until all sixteen bits have been transmitted and the "ENTER DATA" signal 146 returns to a logic low level.

Figure 7:
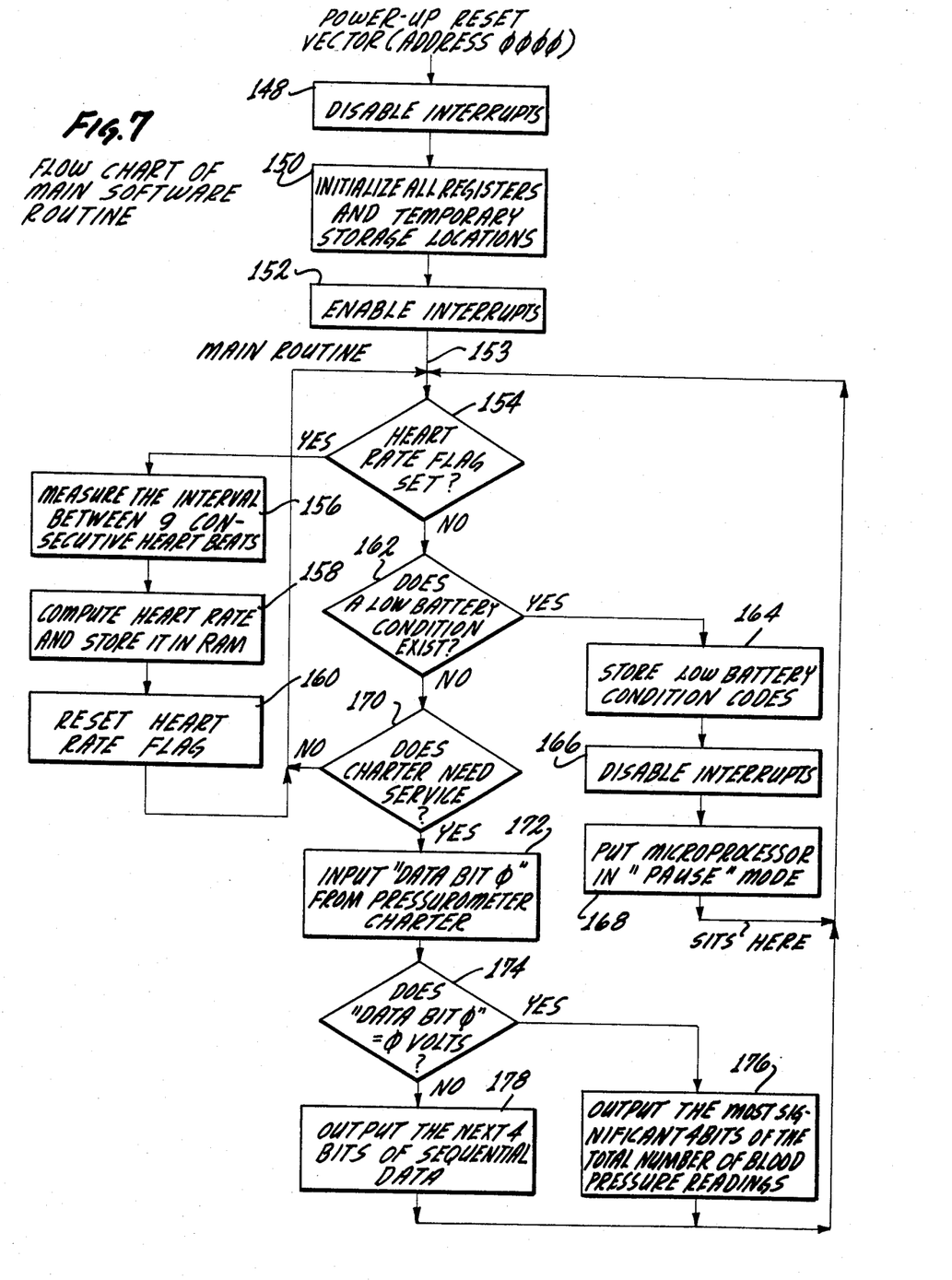
FIG. 7 is a flow chart of the main program used in a preferred embodiment of the present invention.

FIG. 7 is a flow chart of the main program for the microprocessor 60 of the DAS. The program is stored in the PROM 62, which, it will be recalled, is a CMOS fusable-link-programmed memory organized in two blocks or pages of 256×8 bits, for a total of 512×8 bits. The instructions are transmitted from the PROM 62 to the microprocessor 60 over the eight-bit bi-directional bus 66. The operation of the microprocessor is controlled by the program of instructions in the PROM 62, and those instructions are based on the flow charts of FIGS. 7 and 8 in a preferred embodiment.

As shown in FIG. 7, the operation blocks 148, 150, 152 together constitute an initialization subroutine which is initiated by the Power Up Reset Circuit 105, which, it will be recalled, generates a logic low level pulse only when a new battery has been installed in the blood pressure monitoring apparatus 20 and the +7.5 VDC voltage input on the power conductor 104 changes from zero volts to +7.5 VDC. The microprocessor 60 receives this pulse at its "CLEAR" input via the line 106 and executes an internal reset sequence including beginning to execute the program stored in the PROM memory 62 at the address location zero.

Figure 8:
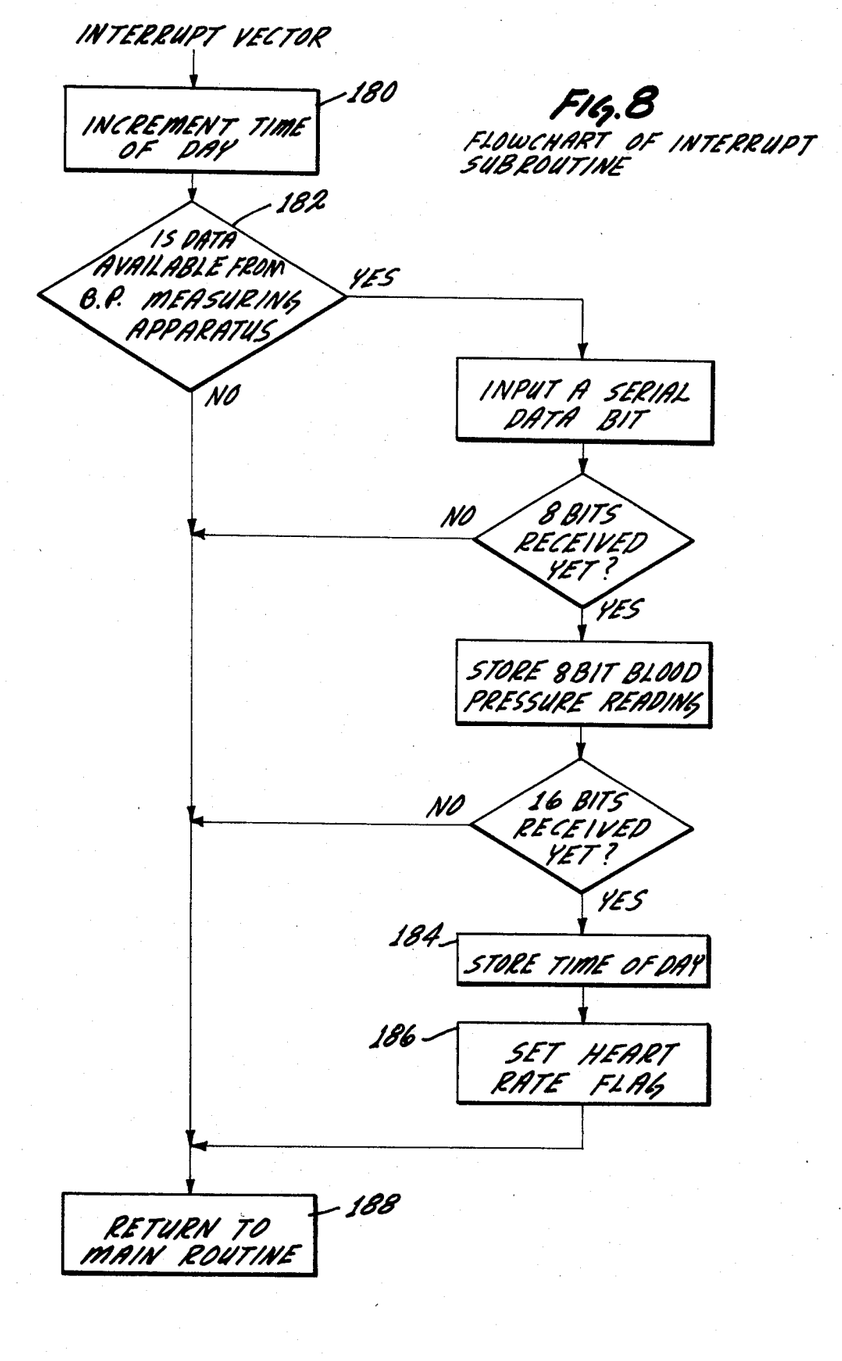
FIG. 8 is a flow chart of an auxiliary routine used in a preferred embodiment of the present invention; and, FIG. 9 is a block diagram showing the present invention in a greater degree of generality.

Upon completion of the initialization operations 148-152, the main routine begins with the decision block 154 which asks whether a heart rate flag is set. As seen in FIG. 8, the heart rate flag is set only after the blood pressure readings have been entered into the RAM 64 from the blood pressure measuring apparatus 20, at which point it becomes necessary to calculate the heart rate based on this most recently received data. If the heart rate flag is set, then it indicates that a new set of blood pressure readings have been received, along with a time-of-day signal, and the program branches to the operation blocks 156, 158 and 160.

As can be seen from these three operation blocks, in a preferred embodiment, the heart rate is calculated by measuring the time interval between nine consecutive heart beats, which is determined by nine successive pulses on the line 126 of FIG. 4. The software contains provision for taking the reciprocal of the time interval in seconds and multiplying it by 540 to obtain the heart rate in beats per minute. It is noted that the operation block 160 resets the heart rate flag, so that the heart rate computation implemented by the blocks 156-160 is not repeated again until another set of blood pressure readings becomes available. Thus, after the operation block 160, the program resumes by returning to the input to the decision block 154. Normally, the blood pressure readings occur only once ever 7.5 minutes, and therefore, on the second pass through the decision block 154 and heart rate flag is found not to be set, and the program therefore proceeds to the decision block 162.

In a preferred embodiment of the invention, the decision block 162 asks the question whether a low battery condition exists. As discussed above, this is determined by the Low Voltage Detect Circuit 86 of FIG. 4 which generates a "LOW POWER" signal on the line 82 when a low battery voltage is detected. If a low battery condition exists, the program branches to the operation blocks 162, 166, 168. These blocks provide for an orderly termination of further microprocessor activities and provide for the application of power to only the CMOS RAM 64 of FIG. 4 to preserve the accumulated data and to the time-keeping circuits to provide for continued running of the time-of-day clock. Once the microprocessor has been put in the "pause mode" by the operation block 168, the program returns to the junction 153 at the beginning of the main routine. If a low battery condition does not exist, the program progresses from the decision block 162 to the decision block 170. In another embodiment of the present invention, the blocks 162, 164, 166, and 168 are eliminated from the flow chart and the orderly termination of further microprocessor activities is initiated and implemented by hardware circuitry.

Figure 6:
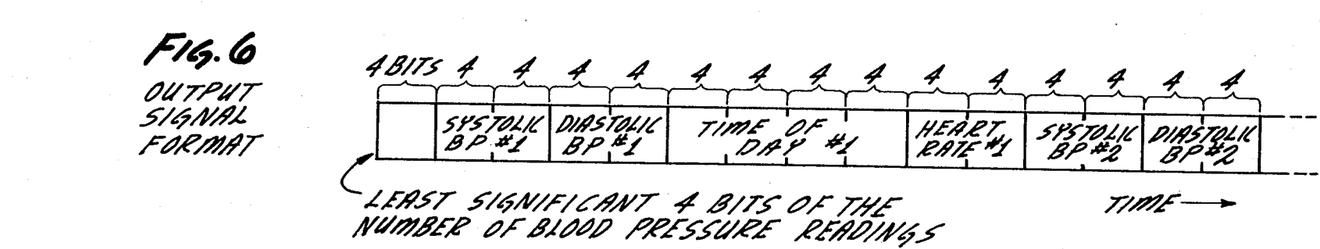
FIG. 6 is a diagram showing the format of the output data signal of the DAS in the embodiment of FIG. 4.

The decision block 180 asks whether the charter 30 has requested service. As described above, this is determined by the presence of a data request signal on the line 90 from the charter 30. More often than not, the charter is not requesting data, and the program returns to the junction 153 at the beginning of the main routine. In the event the charter 30 is requesting service, the program progresses to the blocks 172-178 of FIG. 7. The blocks 172, 172 implement a test to determine whether the transfer of a series of blood pressure readings from the DAS to the charter 30 is already in progress. If the transfer is already in progress, the line 90 of FIG. 4 is at a logic low level and the transfer continues via the block 178. If the transfer has not yet begun, the operation block 176 provides that the charter 30 will be given a number representing the total number of blood pressure readings available for transfer, so the charter 30 can initiate only that number of strobe pulses. FIG. 6 shows the format of the output data transmitted from the DAS to the charter 30.

FIG. 8 is a flow chart of the interrupt subroutine of the program in a preferred embodiment. The initial block 180 increments a clock which is used for keeping track of the time of day. The interrupt subroutine of FIG. 8 is repeated at regular intervals, and thereby serves to keep time. The more frequent flow of the program through the flow chart is from block 180 to block 182 to block 188. However, if blood pressure data is available from the blood pressure measuring apparatus 20 as made known to the microprocessor 60 by the presence of the "ENTER DATA" signal on the line 142, the program branches at the decision block 182 and proceeds to read in, first the eight bits representing the systolic blood pressure, and then another eight bits representing the diastolic reading. When all sixteen bits of the blood pressure readings have been entered, the time of day is stored in the RAM 64 in association with the blood pressure data, and thereafter the heart rate flag is set by the operation block 186. The program returns to the main program of FIG. 7 by virtue of the operation block 188.

Thus, it is seen that the block 186 sets the heart rate flag which, after the program has returned to the main routine of FIG. 7, results in the program's branching at the decision block 154 to the heart rate calculation blocks 156, 158. In an alternative embodiment, additional calculation blocks are inserted between the block 158 and the block 160 to provide for the calculation of a moving average, and the calculation of a derivative, or integral of a stored variable. These additional calculations are made possible by the fact that the time of day associated with the arrival of the blood pressure signals from the blood pressure measuring apparatus 20 is stored in association with those signals by the block 184 of FIG. 8. In the alternative embodiment, after the other variables derived from the basic data have been calculated, the program progresses to the block 160 of FIG. 7 which resets the heart rate flag. The calculated values of the derived variables are stored in the RAM 64 for subsequent application to the charter 30. Alternatively, although heart rate is of considerable interest in the preferred embodiment which is oriented to heart monitoring applications, it is altogether conceivable that the instructions which calculate the heart rate and the preferred embodiment could be replaced by a different set of instructions which operate the microprocessor 60 to calculate a different mathematical function of the received data, including but not limited to, moving averages, derivatives, and integrals.

Figure 9:
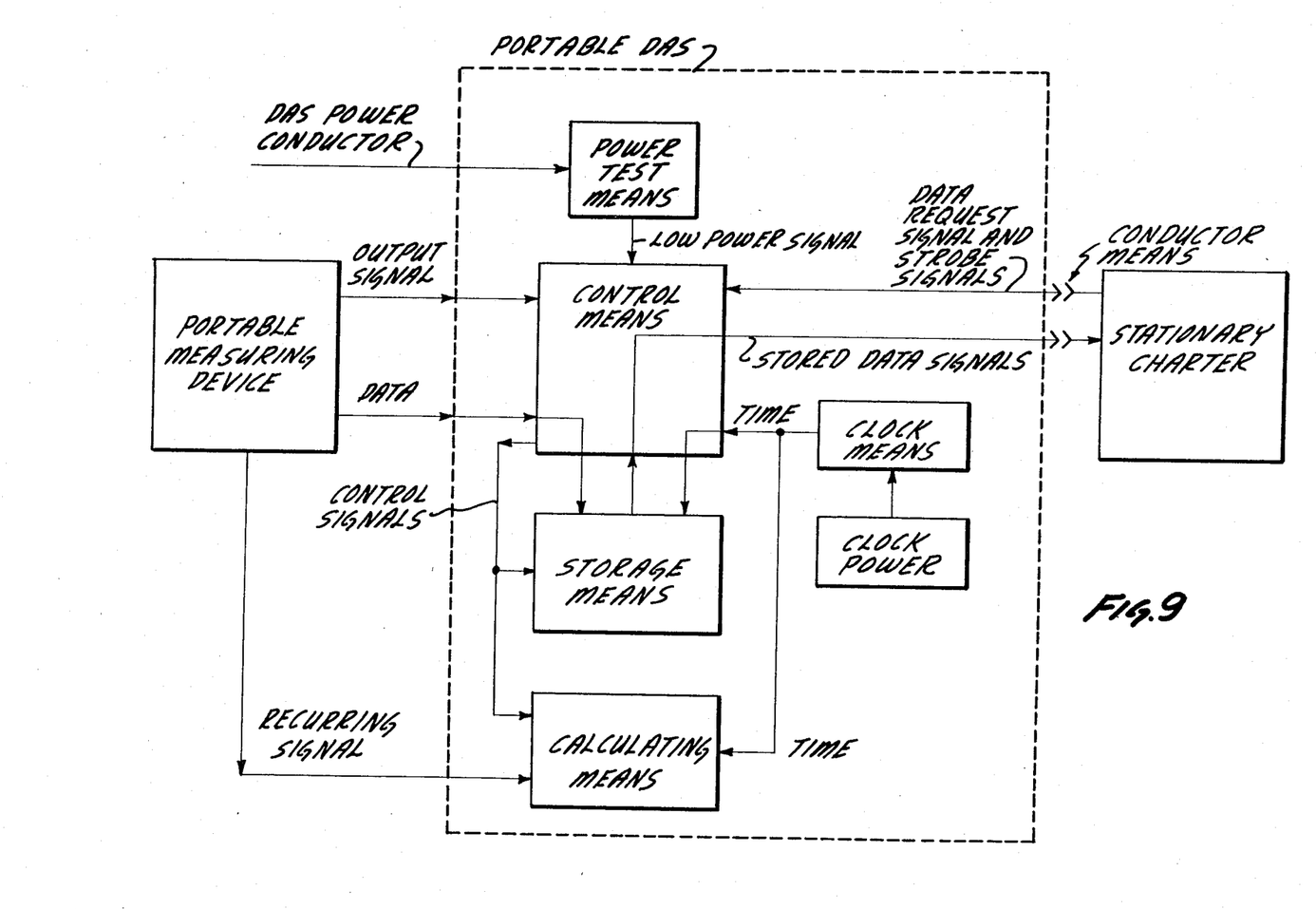

FIG. 9 is a functional block diagram stating the present invention in its broadest expression. FIG. 9 is presented to facilitate the obtaining of an overview of the system and the reading of the claims.

Thus, there has been described a data acquisition and storage system for use with a blood pressure apparatus. Both the DAS and the blood pressure measuring apparatus are portable and are normally worn by the patient. After the ambulatory monitoring session is finished, the DAS is brought to the clinic and connected electrically to a charter, which provides a graphical record of the recorded variables in the form of tables of data and charts. As pointed out above in connection with FIGS. 1 and 2, the DAS of the present invention is a replacement for the magnetic tape previously used to store the data during the ambulatory monitoring session. Unlike the magnetic tape recorder used in the prior art, the DAS of the present invention has no moving parts and is lighter, cheaper, and more reliable.

The DAS of the present invention includes a clock by means of which the time of arrival of each successive word of incoming data is determined, and the times of arrival are stored in association with the data so that the data may be recovered in the proper chronological sequence and the time interval between successive events preserved. In a preferred embodiment, the time-of-day clock continues to run even if the blood pressure measuring apparatus is turned off or disconnected so that the correct time of day will be available when the blood pressure measuring apparatus is subsequently turned on again or plugged in again.

The DAS of the present invention further includes provision for calculating the heart rate of the patient each time a blood pressure reading is obtained, and this data, along with the time of day, is stored with the blood pressure readings.

In a preferred embodiment of the present invention, the DAS includes means to test the voltage of the power source to determine whether it is adequate. If the voltage is found to be low, indicating that the battery is becoming weak, the DAS assumes a dormant mode of operation which prevents erroneous readings from being passed on to the charter, but which preserves the valid readings already stored in the memory of the DAS.

The particular utility of the present invention in connection with ambulatory monitoring of blood pressure and heart rate does not detract from its utility in replacing a portable magnetic tape recorder for the ambulatory monitoring of other physiological variables concerning a patient and his environment. Such variables include without limitation, body and body environment temperatures, body environmental exposures, such as altitude, wind velocity and gamma, X-ray, or infra-red radiation, respiration volume and rate, the concentration of various chemicals in the blood, ECG, EEG, etc. Obviously, the DAS will accept and operate on signals representing any of the aforementioned variables provided the signal has the correct format. Again, in this context, the DAS of the present invention is a very satisfactory substitute for a magnetic tape recorder.

Although a number of alternative embodiments have been pointed out above, a number of additional alternative variations will be obvious to those skilled in the art. Such additional variations are deemed to be within the scope and spirit of the present invention, which is limited only by the following claims.

What is claimed is:

1. A method for creating a long term chronology of a physiological parameter of a patient comprising the steps of:
   coupling a portable, lightweight apparatus to said patient;
   coupling transducers to said patient;
   intermittently sensing said physiological parameter through transducers coupled to said patient and to said apparatus;
   intermittently storing said physiological parameter sensed in a solid state memory included in said apparatus; and
   intermittently storing a time-of-day signal in said memory corresponding to each one of said stored physiological parameters;
   selectively ceasing said storing of said physiological parameter upon a power reduction; and
   continuing said storing of said time-of-day signal during said power reduction,
   whereby said chronology of patient's physiological parameters is created.

2. A method of long-term monitoring physiological parameters and generating time dependent measures in a portable apparatus comprising the steps of:
   intermittently measuring said physiological parameter;
   intermittently storing said physiological parameter in a solid state memory included in said apparatus;
   intermittently storing a corresponding time-of-day data signal in said memory in association with each said stored physiological parameter;
   selectively ceasing said measuring of said physiological parameter upon a lower power condition;
   continuing said storing of said time-of-day data signal during said low power condition;
   retrieving said stored physiological parameters and said corresponding time-of-day signals,
   whereby said stored physiological parameters, said stored time-of-day data signals and said measures comprise a compact chronological history of said measures and parameters in a portable memory having no moving parts.

3. A method for keeping a compact intermittent chronological long-term history of a physiological parameter in a portable apparatus worn by a patient comprising the steps of:
- intermittently measuring said physiological parameter in a solid state memory;
- generating a time-of-day signal in a clock included within said portable apparatus;
- intermittently storing said time-of-day signal in said memory corresponding to measurement of said physiological parameter, said step of measuring performed at the chronological time and date indicated by said time-of-day signal;
- detecting a low power condition in said portable apparatus;
- reducing power consumption in said apparatus without stopping the steps of generating said time-of-day signal and storing said time-of-day signal in memory,
- whereby said compact chronological history, at least with respect to time-of-day data, is kept accurate for when full power and operation is restored in said portable apparatus.

4. An improvement in a method for creating a compact chronological long-term record in a portable apparatus having a solid state memory and circuit for intermittently measuring and storing a physiological parameter in association with a time-of-day signal also stored in said memory, comprising the steps of:
- detecting a lower power condition in said portable apparatus;
- reducing power consumption in said apparatus;
- maintaining adequate power to said memory to fully retain the contents thereof;
- maintaining adequate power to a clock to continue to generate said time-of-day signa; and
- continuing to store said time-of-day signal in said memory to maintain the time-of-day portion of said chronological record during said lower power condition.

5. The improvement of claim 4 wherein the step of reducing power consumption includes ceasing said measurement of said physiological parameter by said circuit.

6. The improvement of claim 4 or 5 further comprising the steps of:
- restoring full power to said portable apparatus; and
- restricting the storing of said physiological parameter corresponding to said time-of-day signal in said memory beginning with the then current state of said time-of-day signal, all prior time-of-day signals previously stored in said memory remaining in said memory.

7. An apparatus for generating a compact chronological long-term record of a physiological parameter comprising:
- a main battery power supply;
- an auxiliary battery power supply;
- a circuit for intermittently measuring said physiological parameter;
- a solid state memory for storing said physiological parameter normally coupled to said main battery power supply;
- a clock means for generating a time-of-day signal and for storing said time-of-day signal in said memory, said clock means normally coupled to said main battery power supply; and
- circuit means for reducing power consumption in said apparatus to maintain information in said memory and to generate said time-of-day signals in said clock means, said circuit means for coupling said auxiliary battery power supply to said memory and time-of-day clock when said main battery power supply fails, said circuit means for ceasing recordation of said physiological parameter and cessation of the storing of new measurements of said physiological parameter in said memory but still maintaining power to said clock means so that time-of-day signal continues to be stored in said memory when said circuit means detects power failure,
- whereby said chronological record is maintained in said memory even during power failure so that when main power is restored to said apparatus, new recordations of said physiological parameter are made in association with accurate time-of-day signals.

8. A method of long-term monitoring of the blood pressure of a patient to provide a compact, portable record of said activity comprising the steps of:
- sensing and measuring said blood pressure of said patient at a predetermined time;
- generating a time-of-day signal;
- storing said measured blood pressure and time-of-day signal in a portable solid state memory as a singular data event;
- inhibiting said steps of sensing and measuring, generating and storing for a predetermined interval;
- resequencing through said steps of sensing and measuring, generating, storing and inhibiting to place a plurality of said data events in said portable solid state memory over a long-term period of time, the number of said steps of resequencing corresponding to the number of data events stored in said portable solid state memory said long-term monitoring equalling at least on day,
- selectively ceasing said resequencing upon a low power condition; and
- continuing said steps of generating, storing and inhibiting said time-of-day signal during said low power condition,
- whereby said compact portable record is provided in said solid state memory during said long-term monitoring.

* * * * *